United States Patent
Solar et al.

(10) Patent No.: US 6,394,995 B1
(45) Date of Patent: May 28, 2002

(54) ENHANCED BALLOON DILATATION SYSTEM

(75) Inventors: Ronald J. Solar, San Diego, CA (US); Thomas Ischinger, Munich (DE); Glen L. Lieber, Poway, CA (US)

(73) Assignee: X Technologies Inc., Orangeburg, NY (US)

( * ) Notice: Subject to any disclaimer, the term of this patent is extended or adjusted under 35 U.S.C. 154(b) by 0 days.

(21) Appl. No.: 09/312,529

(22) Filed: May 14, 1999

Related U.S. Application Data

(60) Provisional application No. 60/085,636, filed on May 15, 1998.

(51) Int. Cl.$^7$ .................. A61M 25/01; A61M 25/02; A61M 25/04; A61M 25/06; A61M 25/08; A61M 25/09; A61M 25/082; A61M 25/085; A61M 25/088; A61M 25/095; A61M 25/098

(52) U.S. Cl. .............. 604/528; 604/103.04; 604/96.01; 606/194

(58) Field of Search ................. 606/192, 194; 604/93.01, 96.01, 264, 265, 507, 509, 104, 523, 528, 907, 912, 913, 915, 918; 128/772

(56) References Cited

U.S. PATENT DOCUMENTS

| | | |
|---|---|---|
| 3,811,448 A | 5/1974 | Morton |
| 4,195,637 A | 4/1980 | Gruntzig et al. |
| 4,323,071 A | 4/1982 | Simpson et al. |
| RE31,800 E | 1/1985 | Lauterjung |
| 4,493,711 A | 1/1985 | Chin et al. |
| 4,573,470 A | 3/1986 | Samson et al. |
| 4,619,263 A | 10/1986 | Frisbee et al. |
| 4,641,649 A | 2/1987 | Walinsky et al. |
| 4,643,186 A | 2/1987 | Rosen et al. |
| 4,748,982 A | 6/1988 | Horzewski et al. |
| 4,762,129 A | 8/1988 | Bonzel |
| 4,790,315 A | 12/1988 | Mueller et al. |
| 4,798,193 A | 1/1989 | Giesy et al. |
| 4,824,435 A | 4/1989 | Giesy et al. |
| 5,003,990 A | 4/1991 | Osypka |
| 5,040,548 A | 8/1991 | Yock |
| 5,045,061 A | 9/1991 | Siefert et al. |
| 5,061,273 A | 10/1991 | Yock |
| 5,090,958 A | 2/1992 | Sahota |
| 5,324,257 A | 6/1994 | Osborne et al. |
| 5,395,332 A | 3/1995 | Resseman et al. |
| 5,413,557 A * | 5/1995 | Solar |
| 5,415,634 A * | 5/1995 | Glynn et al. |
| 5,540,659 A | 7/1996 | Teirstein |
| 5,578,009 A * | 11/1996 | Kraus et al. ........... 604/96 |
| 5,667,493 A | 9/1997 | Janacek |
| 5,667,521 A | 9/1997 | Keown |
| 5,690,642 A * | 11/1997 | Osborne et al. |
| 5,718,680 A | 2/1998 | Kraus et al. |
| 5,728,067 A | 3/1998 | Enger |
| 5,730,698 A | 3/1998 | Fischell et al. |
| 5,863,285 A | 1/1999 | Coletti |
| 5,879,305 A | 3/1999 | Yock et al. |
| 5,882,334 A * | 3/1999 | Sapetka et al. |
| 6,071,285 A | 6/2000 | Lashinski et al. |

* cited by examiner

*Primary Examiner*—Sharon Kennedy
*Assistant Examiner*—Catherine Serke
(74) *Attorney, Agent, or Firm*—Cowan, Liebowitz & Latman, P.C.; William H. Dippert

(57) ABSTRACT

A balloon dilatation system is comprised of an elongated flexible advancement member which terminates in a tubular tracking member slidable over a guidewire. An inflatable balloon has proximal and distal ends, the proximal end communicating with an inflation channel, and the distal end attaching to the tracking member. The balloon portion is coextensive with but not attached to the advancement member.

23 Claims, 5 Drawing Sheets

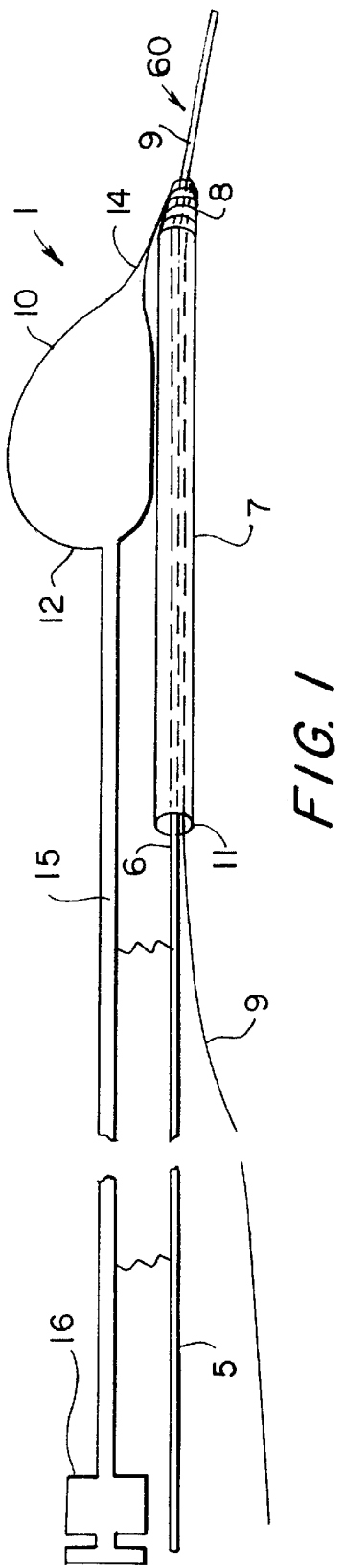
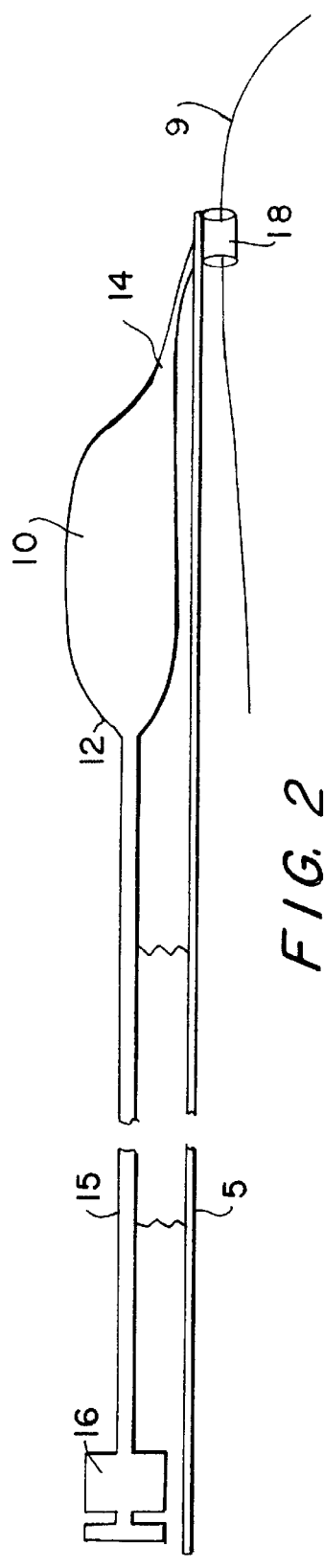

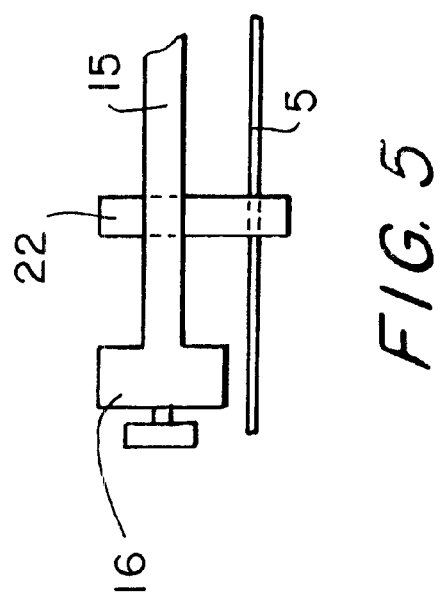
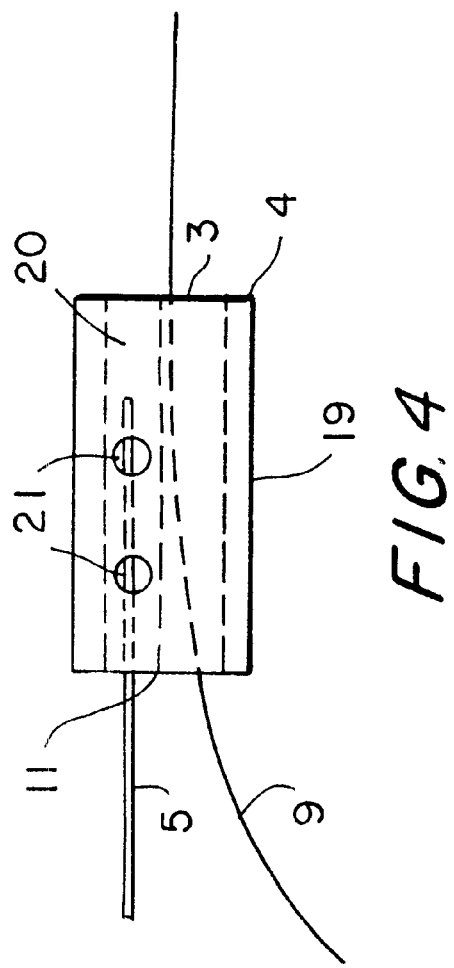

ENHANCED BALLOON DILATATION SYSTEM

This application is based upon co-pending U.S. provisional patent application Ser. No. 60/085,636, filed May 15, 1998.

SCOPE OF THE INVENTION

This invention relates to the field of balloon dilatation. More particularly, this invention relates to improved balloon dilatation systems wherein dilatation balloons are attached to the distal end of advancement means.

BACKGROUND OF THE INVENTION

Balloon dilatation catheters have been used to dilate various types of strictures in blood vessels and other body lumens for over twenty years. Typically, such catheters comprise a balloon mounted on the distal end of an elongated flexible shaft and an inflation tube or lumen extending longitudinally within the shaft from its proximal end to the interior of the balloon. Among the major advancements in balloon dilatation catheters has been the development of smaller catheters that can be used in smaller and/or more distal anatomical locations, and the development of catheters that can be rapidly exchanged. Examples of such catheters are described in U.S. Pat. No. 4,748,982 (Horzewski), U.S. Pat. No. 4,762,129 (Bonzel), U.S. Pat. No. 5,040,548 (Yock), U.S. Pat. No. 5,061,273 (Yock), U.S. Pat. No. 5,569,199 (Solar) and U.S. Pat. No. 5,728,067 (Enger). Because these catheters have become more sophisticated and complex in design, and despite the manufacturers' experience in manufacturing them, these catheters are expensive to make. Furthermore, despite these improvements, difficulties are still encountered in advancing catheters through tortuous anatomy and safely crossing very tight strictures and stenoses in the vascular system and other body lumens or cavities.

Recently vascular stents have been shown to play an important role in reducing the restenosis rates associated with balloon angioplasty. However, stents are sometimes lost from the delivery systems and are difficullt to retrieve safely. In addition, stents cannot completely overcome the trauma and injury that result from balloon dilatation. Thus, there is a need for an enhanced balloon dilatation catheter.

OBJECTS OF THE INVENTION

It is an object of the invention to provide an enhanced dilatation system that is extremely low-profile to more easily and safely cross very tight strictures and stenoses in the vascular system and other body lumens or cavities.

It is also an object of the invention to provide an enhanced dilatation system that provides for an improved means for crossing tight stenoses, as well as to navigate tortuous anatomy.

It is another object of the invention to provide an enhanced dilatation system, that has the ability to be exchanged rapidly.

It is yet another object of the invention to provide an enhanced dilatation system that can be used to retrieve dislodged stents.

It is a further object of the invention to provide an enhanced dilatation system that can be manufactured inexpensively and more reliably then currently available stents.

It is a yet further object of the invention to provide an enhanced dilatation system that has means to dilate stenoses while causing less trauma to the patient.

It is also an object of the invention to provide an enhanced dilatation system allows placement of an additional catheter or instrumentality adjacent to said dilatation catheter.

These and other objects of the invention will become more apparent from the discussion below.

SUMMARY OF THE INVENTION

According to the invention, an enhanced balloon dilatation system comprises an elongated advancement member which terminates in a tubular tracking member, and an inflatable dilatation balloon having proximal and distal ends. The proximal end of the dilatation balloon is in fluid communication with an inflation channel, and the distal end of the dilatation balloon is attached to the tubular tracking member. During advancement of the catheter, the dilatation balloon and inflation channel are somewhat coextensive with, but unattached to, the advancement member. The tubular tracking member is slidable over a guidewire.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which:

FIGS. 1 to 3 are each a schematic, lateral view of an embodiment of the invention;

FIG. 4 is an enlarged illustration of the distal portion of an additional embodiment of the invention;

FIG. 5 is an enlarged illustration of the proximal portion of an alternate embodiment of the invention;

DETAILED DESCRIPTION OF THE INVENTION

Figure 3:
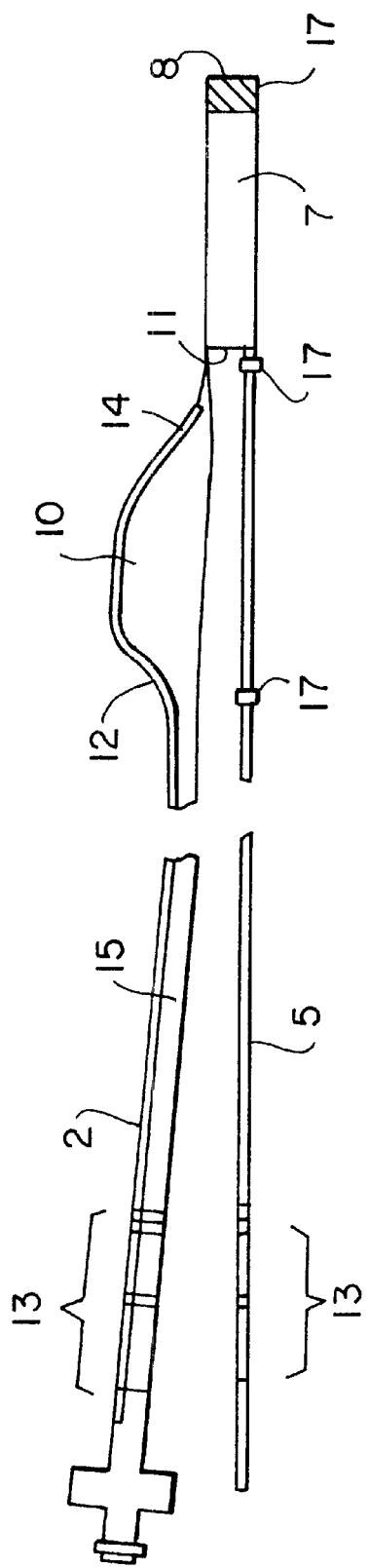

With reference to FIGS. 1 and 3, the enhanced balloon dilatation system, designated generally as 1, has an elongated advancement member 5. Preferably advancement member 5 is formed of a flexible wire or, alternately, of spring hollow hypotubing. Advancement member 5 preferably has a diameter of from about 0.008" to 0.035", which diameter could be larger or smaller depending on the application. Advancement member 5 has sufficient column strength and flexibility to provide for advancement of the catheter through tortuous anatomy. Preferably, advancement member 5 is rigid at its proximal end and becomes increasingly more flexible as it extends distally. This may be accomplished by a number of ways known in the art, including, but not limited to, tapering, selective heat treatment and/or forming advancement member 5 from a composite of materials with various properties.

Advancement member 5 terminates at its distal end 6 in an elongated tubular tracking member 7. Tracking member 7 has a tubular configuration and is adapted to slide over a standard guidewire 9 to allow system 1 to advance easily to a desired location within a patient's body. Tracking member 7 has an open proximal end 11 and an open distal end 8, and is preferably formed of a flexible polymeric tube, a spring coil, or a combination thereof. Tracking member 7 is preferably about 10 to 50 cm long and has an inner diameter that is sized to accommodate guidewire 9, most preferably approximately from about 0.012" to 0.040". Optionally tracking member 7 has an inner, outer, or inner and outer coating with a lubricious material to aid in its movement over the guidewire. Lubricious materials for this purpose are well-known in the art.

Advancement member 5 and tracking member 7 are attached by any suitable means known in the art, such as by fusion or a non-toxic adhesive. Alternatively, advancement member 5 and tracking member 7 may be integrally formed during manufacture.

System 1 also has an inflatable balloon 10 having a proximal end 12 and distal end 14. Distal end 14 of balloon 10 is attached to tracking member 7 by any suitable means known in the art, such as by fusion, adhesive bonding or integral formation, and moves therewith. Distal end 14 of balloon 10 may be attached to distal end 8 of tracking member 7, as shown in FIG. 1, or preferably, distal end 14 of balloon 10 is attached to the proximal end 11 of tracking member 7, as shown in FIG. 3. Balloon 10 is formed of a very thin-walled, preferably less than 0.001" thick, polymeric material. Balloon 10 may be formed of any one of a variety of suitable materials known in the art.

Proximal end 12 of balloon 10 communicates with an elongated inflation channel 15 that extends proximally through a corporeal lumen. Inflation means 15 is formed preferably of a polymeric tubular film that will allow inflation channel 15 to collapse to a smaller profile when not being used for inflation of balloon 10. The wall thickness of inflation channel 15 should preferably be less than 0.001". When inflated, inflation channel 15 will have a diameter of approximately 0.010" or more, depending on the application. Alternatively, inflation channel 15 may be fabricated out of a non-collapsible tubing material as would be familiar to one skilled in this art. As shown in FIG. 3, inflation channel 15 may have position markers 13 on its proximal portion. Position markers 13, which may be applied by ink or other suitable means known in the art, correspond to similar markers on advancement member 5. Such markers provide visual confirmation of concurrent movement of inflation channel 15 and advancement member 5 during advancement and withdrawal of system 1.

Inflation channel 15 has a hub 16 at its opposite, proximal end. Hub 16 is a standard LUER® lock connector that allows connection of inflation means 15 to standard balloon inflator devices or syringes (not shown). By this means, balloon 10 is in fluid communication with an inflator.

As noted above, distal end 14 of inflatable balloon 10 is attached to tubular tracking member 7. In this way, as tubular tracking member 7 travels through the body along the path of guidewire 9, inflatable balloon 10 is pulled along with tracking member 7 to the desired site. However, although balloon 10 lies coextensively with advancement member 5 (FIGS. 2 and 3) and/or tracking member 7 (FIG. 1), it is unattached to advancement member 5. In this most preferred embodiment of least attachment, pushing on advancement member 5 causes balloon 10 to be easily pulled through the anatomy and tight strictures and stenoses. Since the balloon is not being pushed through a stenosis, there is no tendency for the balloon to compress longitudinally and increase in profile and bulk. Such an occurance, which may be found in prior art catheters where the balloon is attached proximally and distally to the catheter shaft, can impede advancement and crossing, as well as result in vascular trauma and clinical complications. Since there is no bulky catheter structure within the interior of the balloon (as is found in prior art catheters), the very thin balloon material can easily fold and conform as required to cross a stenosis with minimal friction and trauma as it is pulled across by the tracking member.

As shown in FIG. 3 a wire 2 can optionally extend at least partially within the inflation channel 15 to the distal end 14 of balloon 10. Wire 2 may provide support to the inflation channel 15 and balloon 10 which may be required in some applications. The support wire may be permanently mounted, or alternatively, it may be removable and used as needed. Also, as shown in FIG. 3, the dilatation system may have radiopaque markers 17 to allow the system's position to be monitored, and the proximal ends of the advancement member 5 and/or inflation channel 15 may have one or more visual markers 13 to indicate the lengths inserted. The radiopaque markers may be comprised of conventional radiopaque materials such as gold or platinum, and the visual markers may be comprised of physiological acceptable inks or coatings, preferably in bright or fluorescent colors.

To summarize use of the preferred embodiment of the present invention, guidewire 9 is first laid in place within a corporeal lumen through any of the means well-known in the art. With use of advancement member 5, tracking member 7 is advanced into the corporeal lumen over guidewire 9. As tracking member 7 is advanced into the corporeal lumen, inflatable dilatation balloon 10 is pulled along with it by virtue of the attachment of distal end 14 of dilatation balloon 10 to either proximal end 11 or distal end 8 of tracking member 7. Once dilatation balloon 10 is in a desired position within the corporeal lumen, dilatation balloon 10 is inflated via inflation means 15 and hub 16.

It is contemplated that tracking member 7 can be varied to provide alternative embodiments of the catheter system 1 of the invention. For example, the length of tracking member 7 may either be made longer or shorter. In the embodiment of the invention shown in FIG. 2, the tracking means has been shortened to a loop 18. Alternatively, it is contemplated that tracking member 7 may extend as an elongated tubular member the full length of system 1, from a proximal position outside the body lumen all the way to distal end 8, to allow fluid administration of the treatment site. Also, the distal end of advancement member 5 could extend distally of tracking member 7. Moreover, in one embodiment of the invention dilatation balloon 10 may be detachable.

In addition, it is contemplated that tracking means 7 may be single-lumen, so that it accommodates only guidewire 9, or it may be multi-lumen, so that it can perform other functions as well. For example, the multi-lumen tracking member 19 shown in FIG. 4 contains lumen 3 for advancing over guidewire 9 and lumen 20, which provides a convenient means for attachment to advancement member 5. Advancement member 5 may be hollow to provide an alternative means for fluid administration to the treatment site. Lumen 20 may be open at the distal end 4 of tracking member 19, and tracking member 19 may alternatively have side holes 21 which provide communication from lumen 20 to the exterior of tracking member 19. Tracking member 19 may also be enlarged and/or lengthened to facilitate perfusion during balloon inflation.

Figure 6:
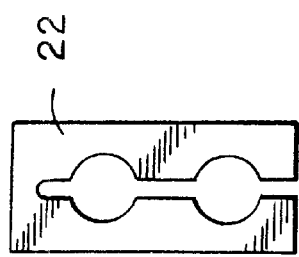
FIG. 6 is a cross-sectional view of a clamping member used in the FIG. 5 embodiment.

It is further contemplated that, in some applications, it may be deemed desirable to provide one or more additional attachment points between the inflation channel and the advancement member at various locations along the advancement member's length. A preferred method of attachment employs a removable clamping member 22 as shown in FIGS. 5 and 6. Clamping member 22 holds inflation channel 15 stationary with respect to advancement member 5 during withdrawal of dilatation system 1. Clamping member 22 is preferably removed or loosened during dilatation system advancement to optimize the pulling forces on the balloon. It is contemplated that in some instances more than one clamp 22 might be used.

Further, it is envisioned that the balloon and the inflation channel may be formed from the same material or they may be formed independently and subsequently attached by suitable known means. In addition, the distal extension of the balloon may be molded or otherwise formed to the shape of the tracking member.

In yet another alternative preferred embodiment of the invention, the advancement member and the tracking member may be formed in multiple segments each having varying mechanical properties which will allow for the customization of the catheter to a particular need.

Figure 7:
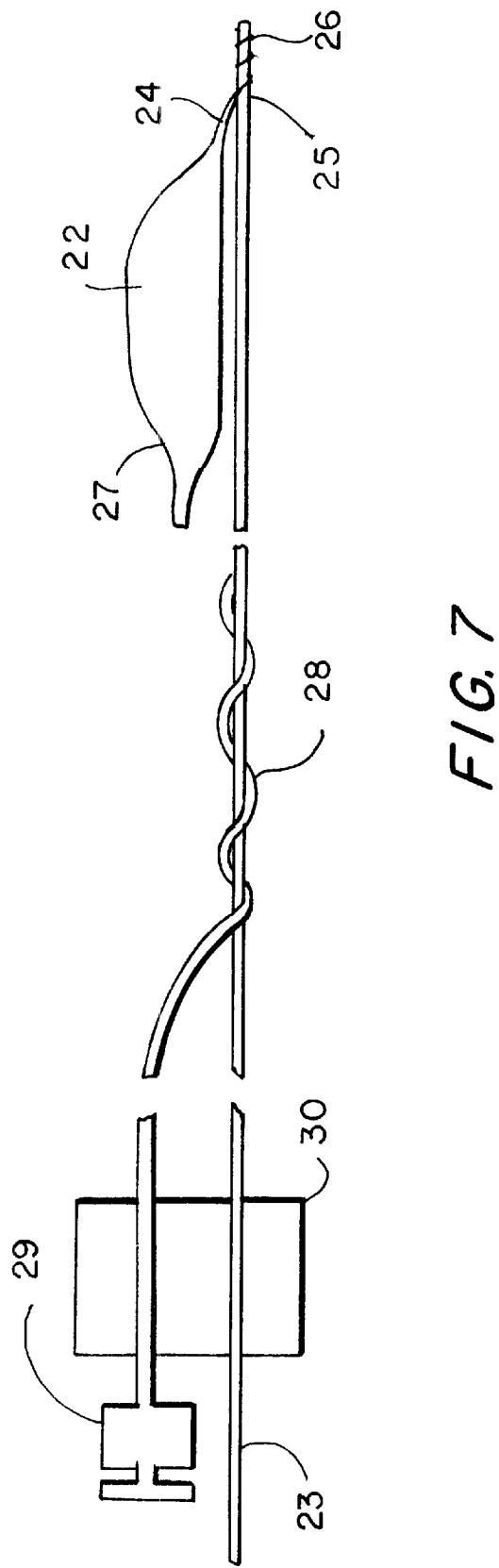

The embodiment of the invention shown in FIG. 7 has a dilatation balloon 22 and a flexible, torqueable, advancement member 23. The distal portion 24 of dilatation balloon 22 is fixedly attached to the distal end 25 of advancement member 23. Advancement member distal end 25 may optionally have a flexible spring tip 26.

The proximal portion 27 of dilatation balloon 22 is in fluid communication with an inflation channel or means 28 having a hub 29 for connection to an inflation source (not shown). Inflation channel 28 preferably is attached to or wound about advancement member 23 in spiral fashion, in such a way to lower the profile of the system but to not interfere with the fluid communication.

A torquer or rotator member 30 may optionally grip the proximal portion of advancement member 23 and inflation channel 28, to allow radial positioning of advancement member 23. In this embodiment it is preferred that the inflation means spirally wrap around the advancement member. Turning the proximal end of the advancement member with torquer 30 will allow distal end 25 of the advancement member 23 to be positioned at a desired radial location relative to dilatation balloon 22 within a corporeal lumen. A torquer 30 could also be used with the embodiments shown in FIGS. 1 and 2, where the tracking means and advancement means would be radially positioned.

The dilation system of the present invention provides the user with a number of significant advantages not otherwise obtainable with currently available catheters. For example, they are less bulky than other available dilatation catheters and thus the balloon is able to move against resistance more easily, which allows less traumatic crossing of restrictions. Also, pushing on the advancement member has the effect of pulling the balloon along through the stenosis, and avoids the problem of bunching or gathering which occurs with other catheters. With a thin film balloon and inflation channel there is no dead space or volume that needs to be evacuated prior to use; therefore, little or no preparation is required. The smaller profile of the dilatation system of the invention allows the dilatation balloon to be passed through stents easily. Partial inflation of the dilatation balloon can grab a previously inserted stent and facilitate retrieval of the stent. The smaller profile also permits passage through displaced stent struts.

Separating the dilatation balloon from a catheter shaft allows greater design flexibility to allow one to provide dilatation systems with improved handling characteristics, and the fewer bonds between the balloon and the advancement shaft results in greater reliability. The simplicity of construction of the system of the present invention results in lower manufacturing costs. For example, fewer bonding operations are required, and expensive balloon folding processes can be avoided. Inflating the balloon against the advancement member or tracking member provides a focused force to enable the user to crack hard lesions at low pressure before the balloon is fully inflated. Doing so would allow vessel stretching to occur at a lower strain rate, which would minimize the trauma associated with balloon dilatation. With the guidewire 9 in place, the balloon can be inflated additionally against the guidewire, thus providing an additional area of focused force.

A further advantage of the present invention is that the design allows additional catheters or devices to be placed adjacent to the dilatation balloon, and to be exchanged without first removing the dilatation system. In this application, the advancement member also acts as an additional guidewire. For example, while balloon catheter 1 is in place within a vascular lesion, a second dilatation system or catheter may be advanced over the advancement member and its balloon positioned along side the first balloon (to increase the effective diameter of the dilatation) or adjacent to the first balloon (to increase the effective length of the dilatation). An imaging catheter such as an intravascular ultrasound catheter may be placed next to the first balloon to access the progress of the treatment without removing the balloon. A drug delivery catheter may be utilized in this manner, and the balloon of system 1 may be inflated at low pressure to provide vascular occlusion to improve the efficacy of the drug delivery. Likewise, various other catheters and devices may be suitably employed.

Figure 8:
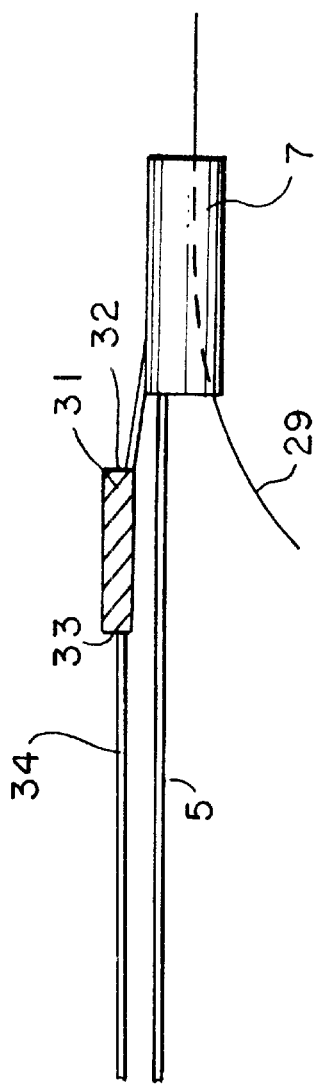
FIGS. 7 and 8 are each a schematic, lateral view of an additional embodiment of the invention.

Although the discussion above has been concerned with balloon dilatation systems and/or catheters, other types of catheters or systems may embody the present invention as schematically illustrated in FIG. 8. In FIG. 8, advancement member 5 terminates in a tubular tracking member 7, which tracks over guidewire 9. Distal end 32 of instrumentality 31 is attached to tracking member 7. Proximal end 33 of instrumentality 31 is unattached to either advancement member 5 or tracking member 7. Instrumentality 31 may be a laser, infusion tube, suction device, atherectomy means, or other therapeutic or diagnostic apparatus. As required, a connecting member 34 may be attached to instrumentality 31. Connecting member 34 may be an electrical conducting wire, optical fiber, tube, or the like.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention, which, as a matter of language, might be said to fall therebetween.

What is claimed is:

1. A balloon dilation system comprising:
    a flexible elongated advancement member having a proximal end and a distal end,
    a tracking member having a proximal end and a distal end, said tracking member being adapted to slide over a guidewire and being fixedly attached to the distal end of the advancement member,
    an inflation channel, and
    an inflatable dilation balloon having a proximal end and a distal end, the proximal end of the balloon being in fluid communication with the inflation channel, wherein only the distal end of the balloon is attached to the tracking member and wherein the advancement member is external to the balloon.

2. The dilatation system of claim 1, wherein the tracking member comprises two or more lumens.

3. The dilatation system of claim 1, wherein the dilatation balloon is attached to the distal end of the tracking member.

4. The dilatation system of claim 1, wherein the dilatation balloon is attached to the proximal end of the tracking member.

5. The dilatation system of claim 1, wherein the tracking member has a lubricious coating.

6. The dilatation system of claim 1, wherein the tracking member is formed integral with the dilatation balloon.

7. A balloon dilatation system comprising:
   a flexible elongated advancement member having a proximal end and a distal end,
   a dilatation balloon having a proximal end and a distal end, and
   an inflation channel, the proximal end of the balloon being in fluid communication with the inflation channel,
   wherein only the distal end of the balloon is attached to the distal end of the advancement member and wherein the advancement member is external to the balloon.

8. The dilatation system of claim 1 or 7, wherein the inflation channel is substantially coextensive with the advancement member.

9. The dilatation system of claim 1 or 7, wherein the inflation channel is in a spiral configuration around the advancement member.

10. The dilatation system of claim 1 or 7, wherein the advancement member comprises a flexible wire or hypotubing.

11. The dilatation system of claim 1 or 7, wherein the advancement member is rigid at its proximal end and the advancement member is increasingly more flexible as the advancement member extends distally.

12. The dilatation system of claim 1 or 7, wherein the inflation channel is collapsible or noncollapsible.

13. The dilatation system of claim 1 or 7, wherein the dilatation balloon or the inflation channel, or both, have a wire reinforcement.

14. The dilatation system of claim 1 or 7, wherein the dilatation balloon and the inflation channel are formed integral.

15. The dilatation system of claim 1 or 7, wherein the inflation channel is attached to the advancement member at at least one point.

16. The dilatation system of claim 1 or 7, which also comprises a torquer attached to the proximal end of the advancement member.

17. The dilatation system of claim 1 or 7, wherein the balloon and the inflation channel are unattached to the advancement member.

18. The dilatation system of claim 1 or 7, wherein the balloon and/or the inflation channel are attached to the advancement member.

19. A method of positioning the distal end of a balloon dilatation catheter at a desired location within a patient's body, which comprises the step of:
   advancing a dilatation system of claim 1 or 7 through a corporeal lumen so that the distal end of said balloon dilatation catheter is positioned at a desired location.

20. The method of claim 19, wherein another dilatation system or other medical device is advanced distally over the dilatation system of claim 1 or 7.

21. A medical delivery system comprising:
   a flexible elongated advancement member having a proximal end and a distal end,
   a tracking member having a proximal end and a distal end, said tracking member being adapted to slide over a guidewire and being fixedly attached to the distal end of the advancement member, and
   a medical instrument or device or a portion thereof having a proximal end and a distal end, the proximal end of the instrument or device being in communication with a source,
   wherein only the distal end of the medical instrument or device is attached to the tracking member or the advancement member and wherein the advancement member is external to the medical instrument or device or a portion thereof.

22. A balloon dilation system comprising:
   a flexible elongated advancement member having a proximal end and a distal end,
   a tracking member comprising two or more lumens and having a proximal end and a distal end, said tracking member being adapted to slide over a guidewire and being fixedly attached to the distal end of the advancement member,
   an inflation channel, and
   an inflatable dilatation balloon having a proximal end and a distal end, the proximal end of the balloon being in fluid communication with the inflation channel,
   wherein only the distal end of the balloon is attached to the tracking member and wherein the advancement member is external to the balloon.

23. A balloon dilatation system comprising:
   a flexible elongated advancement member having a proximal end and a distal end,
   a tracking member having a proximal end and a distal end, said tracking member having a lubricious coating, being adapted to slide over a guidewire, and being fixedly attached to the distal end of the advancement member,
   an inflation channel, and
   an inflatable dilatation balloon having a proximal end and a distal end, the proximal end of the balloon being in fluid communication with the inflation channel,
   wherein only the distal end of the balloon is attached to the tracking member and wherein the advancement member is external to the balloon.

* * * * *